(12) United States Patent  (10) Patent No.: US 7,592,914 B2
Sakama et al.  (45) Date of Patent: Sep. 22, 2009

(54) RADIO FREQUENCY IDENTIFICATION TAG AND MANUFACTURING METHOD THEREOF

(75) Inventors: Isao Sakama, Hiratsuka (JP); Minoru Ashizawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 189 days.

(21) Appl. No.: 11/324,358

(22) Filed: Jan. 4, 2006

(65) Prior Publication Data

US 2007/0046466 A1  Mar. 1, 2007

(30) Foreign Application Priority Data

Aug. 25, 2005  (JP) ............... 2005-244613

(51) Int. Cl.
G08B 13/14 (2006.01)
(52) U.S. Cl. .............. 340/572.1; 340/572.4; 340/572.7; 340/572.8; 340/568.2; 235/491; 235/492; 235/380
(58) Field of Classification Search .............. 340/572.1, 340/572.4, 572.7, 572.8, 568.2; 235/491, 235/492, 380
See application file for complete search history.

(56) References Cited

U.S. PATENT DOCUMENTS 7,201,328 B2* 4/2007 Usami et al. ................. 235/492
7,397,378 B1* 7/2008 Leason ...................... 340/572.7
2002/0167450 A1 11/2002 Korden et al.
2007/0139205 A1* 6/2007 Tanaka et al. ............. 340/572.8
2007/0251993 A1* 11/2007 Masuta ....................... 235/380

FOREIGN PATENT DOCUMENTS

| EP | 1538560 | 6/2005 |
| EP | 1548674 | 6/2005 |
| JP | 2002-358494 | 12/2002 |
| WO | 0205039 | 1/2002 |

* cited by examiner

*Primary Examiner*—Tai T Nguyen
(74) *Attorney, Agent, or Firm*—Brundidge & Stanger, P.C.

(57) ABSTRACT

A tablet PTP package contains a multiplicity of tablets by a resin PVC and a metal sheet such as an aluminum sheet. An elongate space pattern is formed in a part of the aluminum sheet on the lower surface of the package to form an island area constituting an antenna. A small radio IC inlet including an IC chip mounted on a small antenna is arranged on the reverse surface (upper surface of the package) of the portion of the aluminum sheet corresponding to the island area. The small radio IC inlet and the second antenna formed by the island area are electrostatically coupled to each other with the resin PVC as a dielectric member, and thus a RFID (radio frequency identification) tag is configured.

23 Claims, 11 Drawing Sheets

FIG.1A
UPPER SURFACE (PVC SURFACE) OF PACKAGE

FIG.1B
LOWER SURFACE (ALUMINUM SURFACE) OF PACKAGE

(a) BASIC FORM (UNIDIRECTIONAL POLARIZATION)

ISLAND PATTERN OF $\lambda/2$ OPERATION

↓ MODIFY

(b) MODIFICATION 1 (UNIDIRECTIONAL POLARIZATION)

ISLAND PATTERN OF $\lambda/4$ OPERATION

↓ MODIFY

(c) MODIFICATION 2 (BIDIRECTIONAL POLARIZATION)

$\lambda/2$ OPERATION

(d) MODIFICATION 3 (BIDIRECTIONAL POLARIZATION)

$\lambda/4$ OPERATION

(e) MODIFICATION 4 (BIDIRECTIONAL POLARIZATION)

$\lambda/2$ OPERATION

FIG.11
SLOT LENGTH AND COMMUNICATION DISTANCE

FIG.12
INLET MOUNTING POSITION OF SLOT AND COMMUNICATION DISTANCE

FIG.13A

6 ISLAND AREA  5 SPACE PATTERN

9(4)  9(1)  9(2)  9(3)

FIG.13B 5   100 PENINSULAR AREA

RADIO FREQUENCY IDENTIFICATION TAG AND MANUFACTURING METHOD THEREOF

INCORPORATION BY REFERENCE

The present application claims priority from Japanese application JP 2005-244613 filed on Aug. 25, 2005, the content of which is hereby incorporated by reference into this application.

BACKGROUND OF THE INVENTION

This invention relates to a radio frequency identification tag (RFID tag) for transmitting the information recorded in an IC chip by radio communication, or in particular to a "RFID tag" mounted on the surface of a metal sheet and a "RFID tag" manufacturing method.

In recent years, a "RFID tag" has come to find wide applications for information control of articles and structures or distribution control. The "RFID tag" is configured of a small IC chip having recorded information therein and a small antenna for transmitting the information in the IC chip by radio communication. The "RFID tag" is used by being attached to an article or buried in a structure. The IC chip is as small as about 0.4 mm×0.4 mm size by 0.1 mm high. By bringing a reader-writer in proximity to this "RFID tag", the information (i.e. the information on the attributes of individual articles and structures) recorded in the IC chip can be read without contact. Considering the manufacturing cost and the mounting ease, the "RFID tag" is preferably as small and lightweight as possible.

A "RFID tag" is available, for example, in which on a first antenna connected to an IC chip, a second antenna (auxiliary antenna) is arranged through a second spacer of a dielectric material, and by increasing the radio intensity utilizing the amplification due to the resonance of the second antenna, the communication distance can be increased even in the presence of considerable amount of metal or moisture. Also, a technique is known in which a slot antenna is formed on the surface of a metal plate and brought into contact with a terminal of the IC chip as a metal, thereby achieving superior antenna characteristics even on the surface of a metal plate (JP-A-2002-358494, Paragraphs 0009 to 0018 and FIGS. 1 to 3).

In recent years, application of the "RFID tag" to information control of medicine in such forms as tablets and capsules has been desired as well as general articles or structures. The medicines in the form of tablets and capsules are sealed in PTP (Press Through Package) which is a kind of heat sealed package. One surface of the package is covered entirely by a resin sheet such as PVC in the thickness of 0.2 to 0.25 mm, and the other surface is entirely covered by an aluminum sheet. The aluminum sheet reduces the communication distance, and therefore the ordinary "RFID tag" cannot be used, a "RFID tag" compatible with a metal is required. The use of a "RFID tag" suitable for a metal, however, would increase the size and cost of the package and therefore not suitable for packaging medicines in general.

SUMMARY OF THE INVENTION

This invention has been developed in view of the problems described above, and the object thereof is to provide a "RFID tag" having a long communication distance with a small radio IC inlet without any additional component elements on the package sealed by a metal film of aluminum or the like.

In order to achieve the object described above, according to this invention, there is provided a "RFID tag" for transmitting the information recorded in an IC chip by radio communication, comprising an inlet including the IC chip mounted on a small antenna formed with a slit for impedance matching, and an antenna (hereinafter sometimes referred to as the second antenna) implemented by a space pattern formed on the surface of a metal foil, wherein the inlet is mounted on the surface of the antenna, the space pattern forms an antenna as an island area isolated from the other area on the surface of the metal foil, and the antenna formed by the island area has an electrical length of $\lambda/2$, where $\lambda$ is the wavelength of the radio wave radiated from the small antenna.

The space pattern may alternatively form a second antenna by a peninsular area surrounded by a U-shaped groove formed on the surface of the metal foil. In this case, the antenna formed by the peninsular area has an electrical length of $\lambda/4$. As another alternative, the space pattern may implement a second antenna by forming a slot having a predetermined length and width on the surface of a metal foil. In this case, the length of the slot formed on the surface of the metal foil has an electrical length of $\lambda/2$ or $\lambda/4$ for unidirectional polarization.

According to this invention, an inlet is prepared in which an IC chip is mounted on a small antenna formed with an impedance matching circuit. This inlet is mounted on an antenna implemented by a slot or an island area formed on an aluminum sheet of a package thereby to realize a "RFID tag". As a result, the inlet itself can function as a small "RFID tag" on the one hand, and the radio wave is amplified by the operation of the antenna formed on the aluminum sheet on the other hand. Even a "RFID tag" mounted on the metal surface, therefore, can radiate a strong radio wave. Thus, a "RFID tag" mounted on the aluminum sheet package can secure a long communication distance.

Other objects, features and advantages of the invention will become apparent from the following description of the embodiments of the invention taken in conjunction with the accompanying drawings.

BRIEF DESCRIPTION OF THE DRAWINGS

FIGS. 1A and 1B are diagrams showing the external appearance of a tablet PTP package with a "RFID tag" mounted thereon according to a first embodiment of the invention, in which

DETAILED DESCRIPTION OF THE INVENTION

In the "RFID tag" according to the invention, a space pattern of the desired shape is formed on the surface of a seal of a metal thin film (aluminum seal, for example) and an island antenna area isolated from the remaining aluminum seal area or a peninsular area partly isolated from the remaining aluminum seal area is formed. A small radio IC inlet is mounted in the island or peninsular antenna area, and an element configured of the island or peninsular antenna area and the small radio IC inlet is defined as a "RFID tag" according to the invention. The small radio IC inlet may be a small inlet having an antenna about 0.1 λ long capable of communication with a reader-writer, for example, with a microwave of 2.45 GHz band. The antenna of the small inlet is 1.5 mm wide and 10 mm long. As an alternative, the "RFID tag" according to the invention can be realized also by forming a slot by the space pattern, and mounting the small radio IC inlet over the slot.

According to this embodiment, the element configured of a small antenna formed with an impedance matching circuit (i.e. a slit) and an IC chip mounted over the slit of the small antenna for recording information is defined as a small radio IC inlet (referred to simply as an inlet in the claims), and the component element including the small radio IC inlet mounted in the antenna area formed as an island or peninsula on the seal of a metal thin film is defined as a "RFID tag".

In this configuration, the desired "RFID tag" can be formed by mounting the small radio IC inlet on the package of a metal thin film of aluminum etc. as a seal member without adding a new component element. In the "RFID tag" according to this embodiment, the small radio IC inlet carrying the IC chip is arranged in the antenna area formed on the package such as an aluminum seal. In view of the large margin of position accuracy of the small radio IC inlet, i.e. in view of the fact that the small radio IC inlet can be arranged at an approximate position, a highly accurate application machine is not required and therefore the mass productivity of the package is high.

The "RFID tag" according to several embodiments is explained in detail below with reference to the drawings. In the embodiments described below, the "RFID tag" mounted on the tablet PTP package is taken as an example.

FIRST EMBODIMENT

Figure 1A:
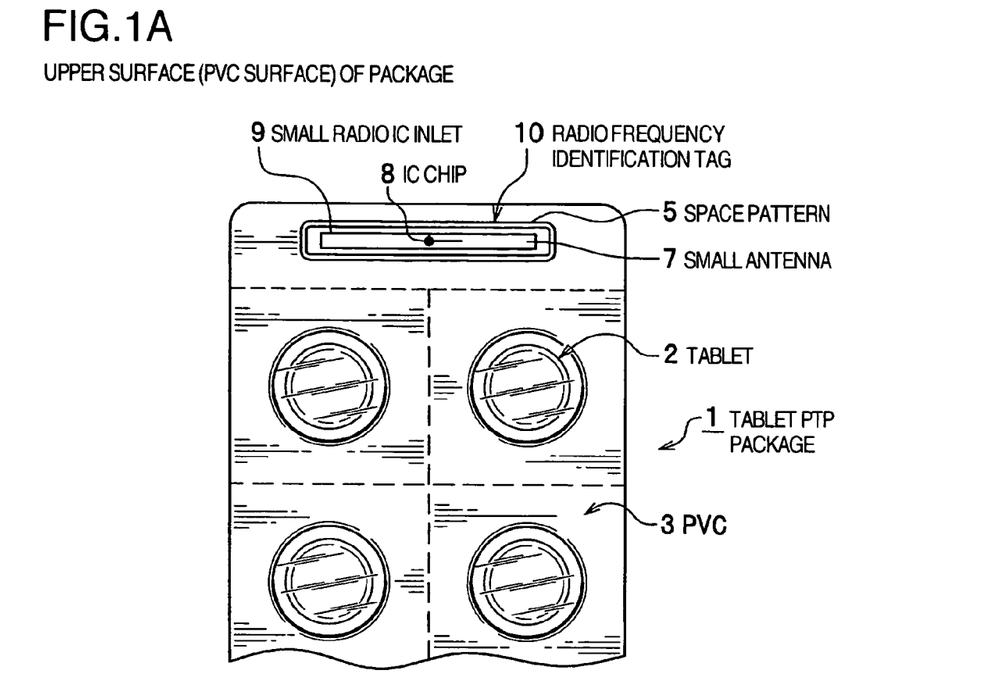
FIG. 1A shows the upper surface (PVC surface) of the package, and FIG. 1B the lower surface (aluminum surface) of the package.
Figure 1B:
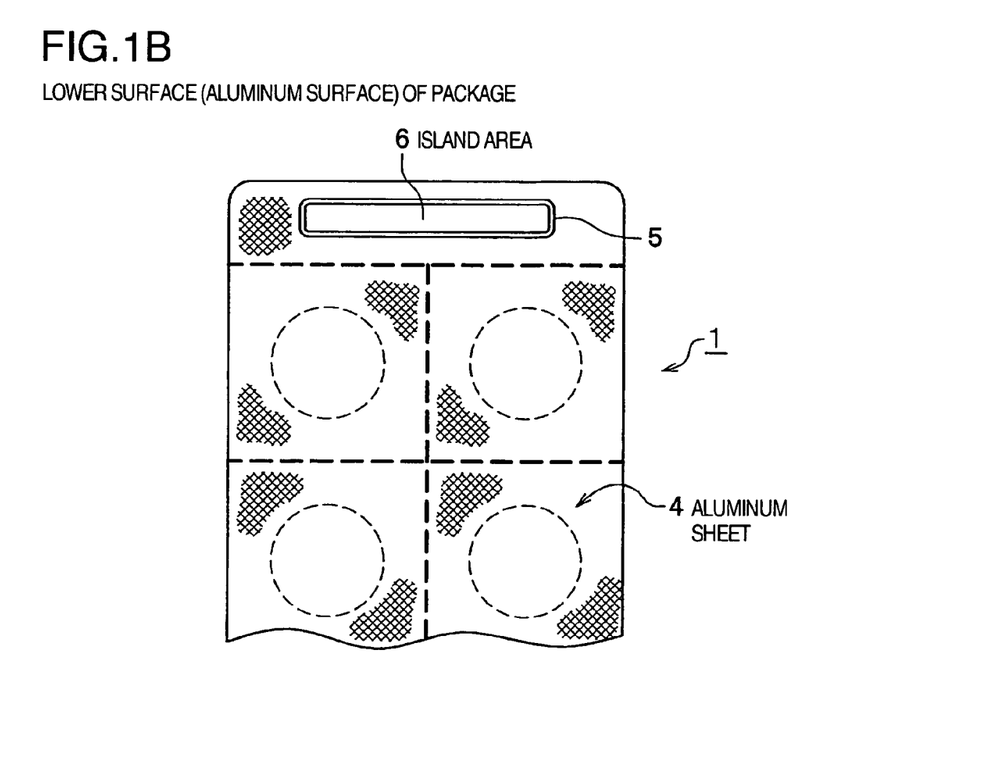

FIGS. 1A and 1B show the appearance of the tablet PTP package with the "RFID tag" mounted thereon. FIG. 1A shows the upper surface (PVC surface) of the package, and FIG. 1B the lower surface (aluminum surface) thereof. As shown in FIGS. 1A and 1B, the tablet PTP package 1 includes a multiplicity of tablets 2 packed by a PVC 3 and an aluminum sheet 4. As shown in FIG. 1B, an elongate space pattern 5 is formed in a part (upper part, for example) of the aluminum sheet 4 on the lower surface of the package thereby to form an island area 6 constituting an antenna area. Also, as shown in FIG. 1A, a small radio IC inlet 9 with an IC chip 8 mounted on a small antenna 7 is arranged on the reverse surface of the portion of the aluminum sheet 4 (i.e. the upper surface of the package) formed with the island area 6. Specifically, the small radio IC inlet 9, as shown in FIG. 1A, is arranged on the surface of the PVC 3 on the upper surface of the package.

The antenna area and the small radio IC inlet 9 formed by the island area 6 in the space pattern 5, therefore, are electrostatically coupled to each other with the resin PVC 3 as a dielectric unit. Thus, the antenna area and the small radio IC inlet 9 constituting the island area 6 make up the "RFID tag" 10. The small radio inlet 9 is fixed on the island area 6 by an acrylic adhesive 0.07 mm thick. A reader-writer not shown, when brought in proximity to the the "RFID tag" 10 of the tablet PTP package 1 configured this way, receives the radio wave of normal strength radiated from the "RFID tag" 10 and can read the information on the tablets contained in the tablet PTP package 1.

In the process, the small radio IC inlet 9, though as small as 0.1 λ capable of communication with the reader-writer by a microwave of 2.45 GHz band, radiates a strong radio wave due to the antenna function of the antenna area made up of the island area 6. Therefore, the radio strength is not weakened by the aluminum sheet 4 outside the island area 6. Specifically, according to this embodiment, the provision of the space pattern 5 on the packaging aluminum sheet 4 prevents the reduction in communication distance which otherwise might occur due to the metal surface while at the same time lengthening the communication distance by utilizing the packaging aluminum sheet 4 as an antenna due to the island area 6 isolated by the space pattern 5.

Figure 2:
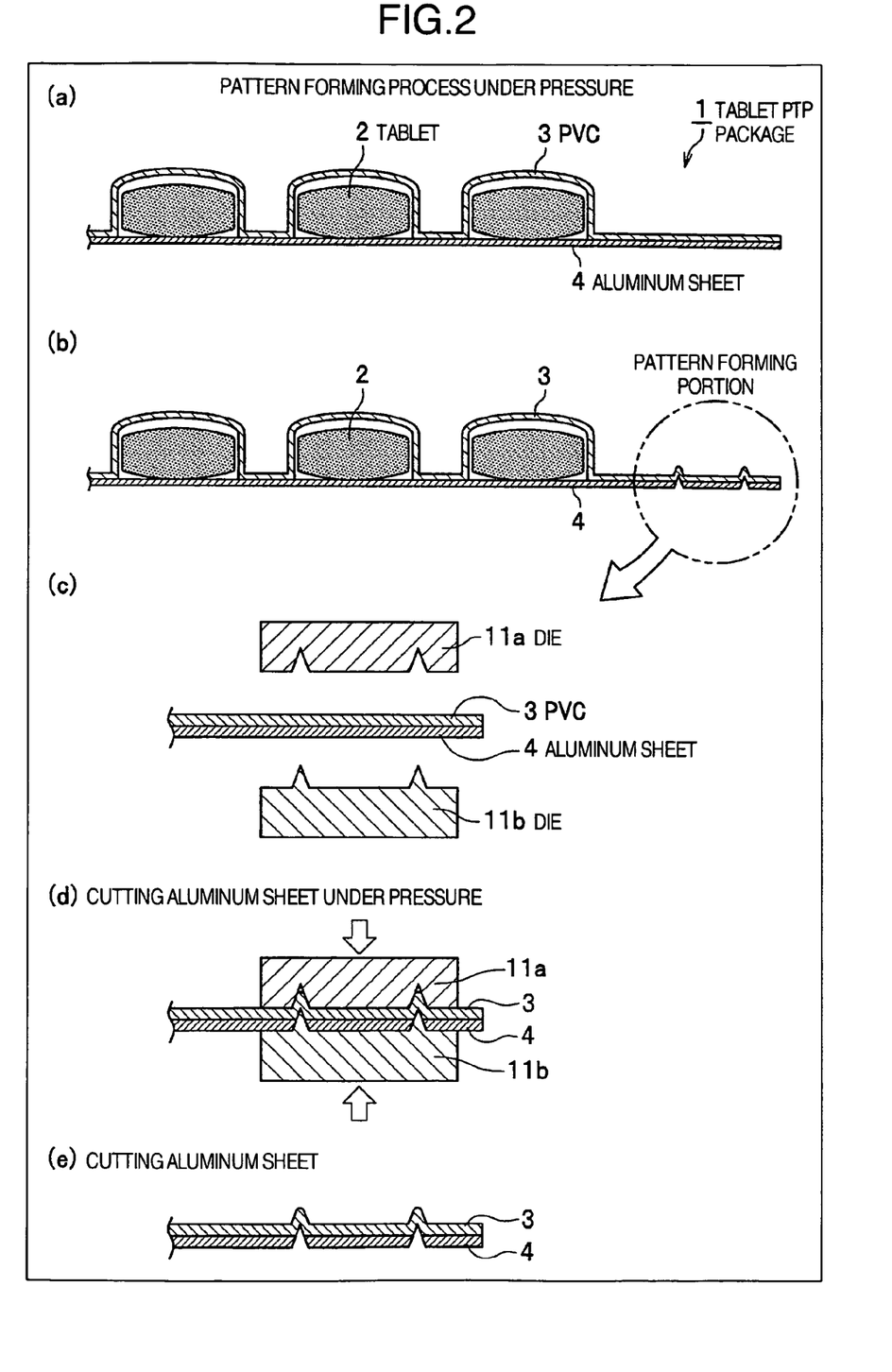
FIG. 2 is a process diagram showing the steps of realizing the tablet PTP package shown in FIG. 1 by forming a space pattern under pressure.

FIG. 2 is a diagram showing the steps of fabricating the tablet PTP package shown in FIG. 1 by forming a space pattern under pressure. As shown in FIG. 2(a), a pattern forming portion shown in FIG. 2(b) is arranged by patterning under pressure in the tablet PTP package 1 with the tablets 2 packed by the PVC 3 and the aluminum sheet 4.

The pattern forming portion shown in FIG. 2(b) is created in such a manner that as shown in FIG. 2(c), a lamination of the PVC 3 and the aluminum sheet 4 is inserted between a die 11a and a die 11b, and as shown in FIG. 2(d), the aluminum sheet 4 is cut off under the pressure applied between the dies 11a and 11b. As a result, as shown in FIG. 2(e), the aluminum sheet 4 is cut off and protrusions are formed on the PVC 3. By using the force of the dies in this way, the space pattern 5 shown in FIGS. 1A, 1B is formed. Then, using the resin protrusions of the PVC 3 as a guide, the small radio IC inlet 9 is mounted.

Figure 3A:
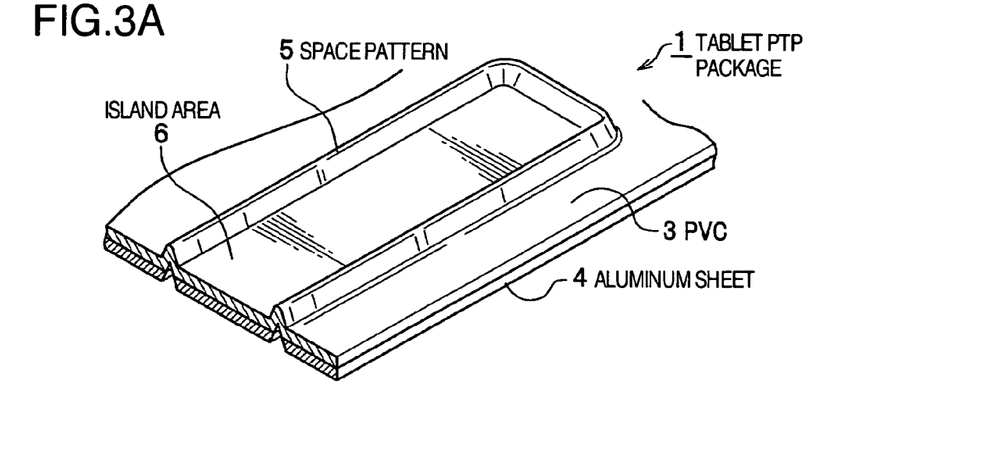
FIGS. 3A, 3B and 3C are perspective views schematically showing the manner in which a space pattern is formed under pressure and the manner in which the small radio IC inlet is mounted as shown in FIG. 2.
Figure 3B:
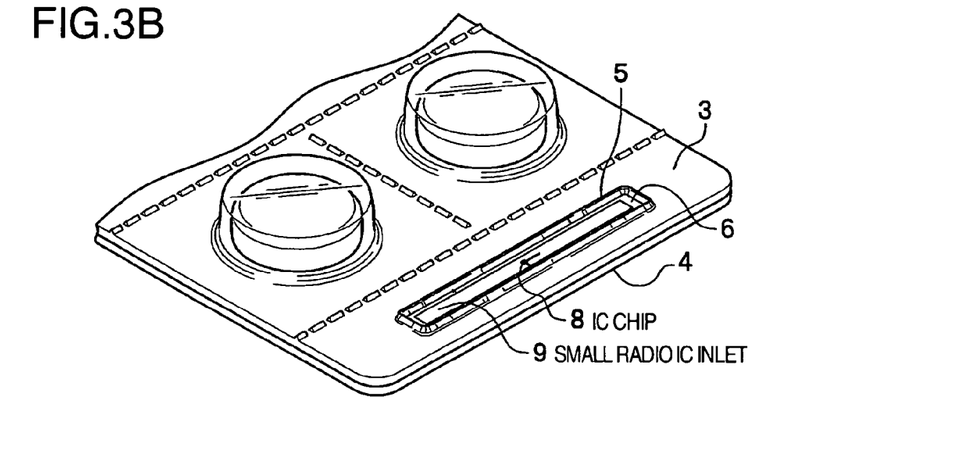
Figure 3C:
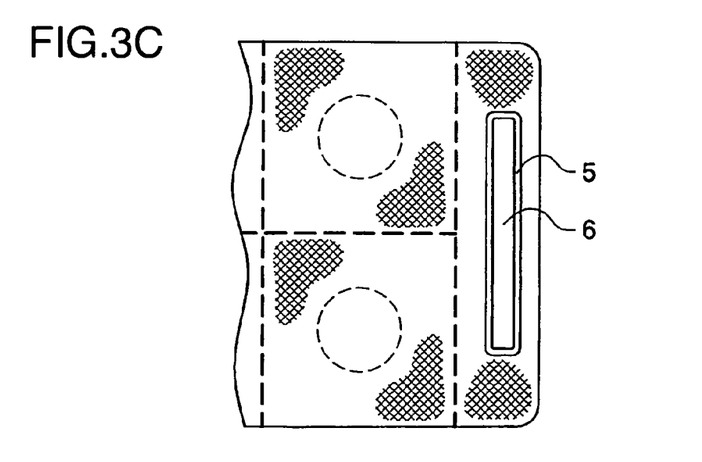

FIGS. 3A to 3C are perspective views schematically showing the manner in which the space pattern is formed under pressure as shown in FIG. 2 and the small radio IC inlet 9 is mounted. As shown in FIG. 3A, the tablet PTP package 1 is produced by cutting off the aluminum sheet 4 along the space pattern 5, forming the PVC 3 with protrusions and forming the island area 6 of the aluminum sheet 4 as an antenna area. As shown in FIG. 3B, the small radio IC inlet 9 with the IC chip 8 mounted thereon is arranged on the surface portion of the PVC 3 corresponding to the island area 6. Specifically, the island area 6 making up the antenna area and the small radio IC inlet 9 are electrostatically coupled to each other through the resin PVC 3. As shown in FIG. 3C, the island area 6 is isolated by the space pattern 5 as an independent area, and therefore can constitute an independent antenna area.

SECOND EMBODIMENT

Figure 4:
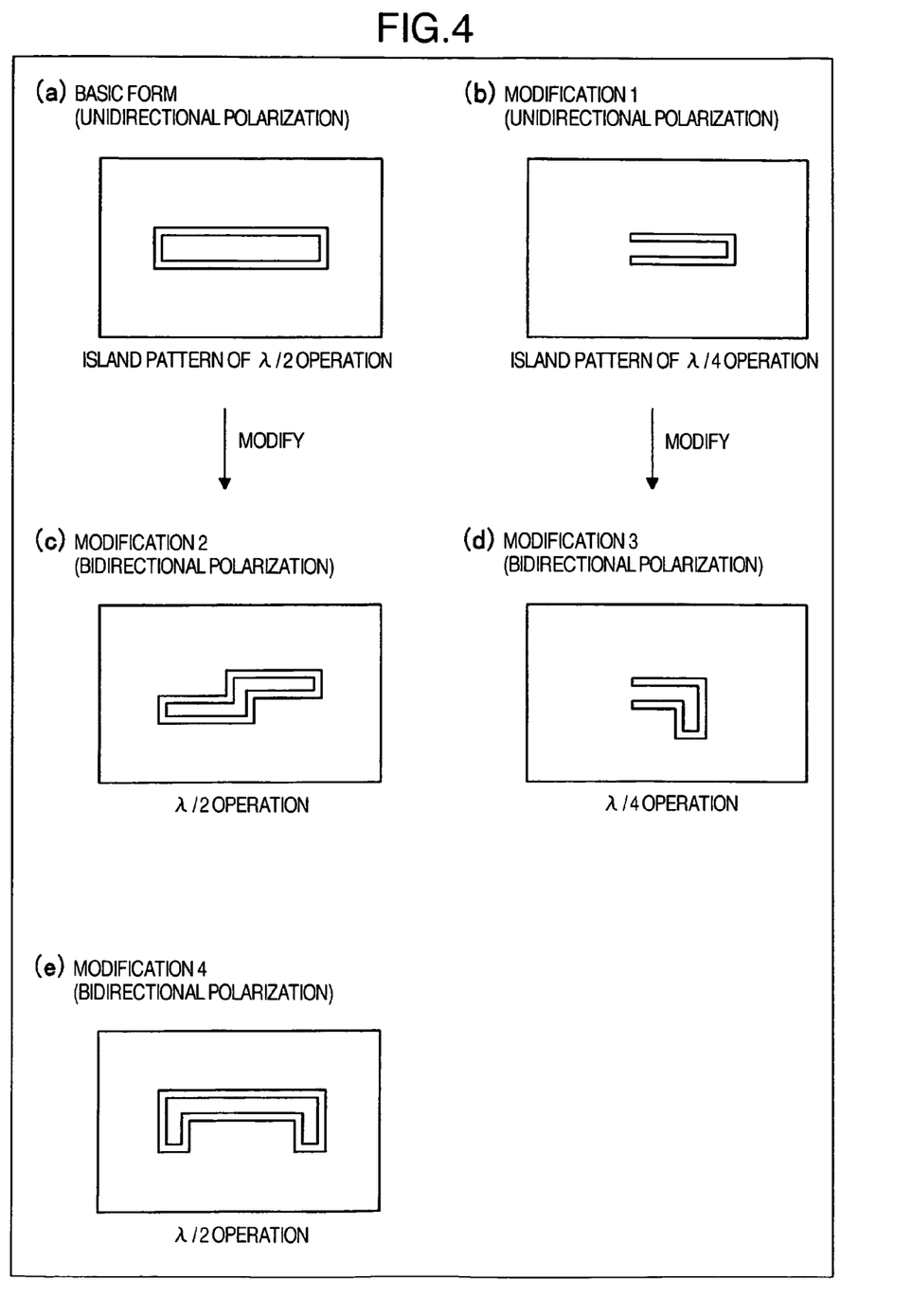
FIG. 4 is a diagram showing variations of the space pattern of the island area or the peninsular area formed on the aluminum sheet of the tablet PTP package according to a second embodiment of the invention.

As a second embodiment of the invention, variations of the space pattern forming an island area or a peninsular area are explained. FIG. 4 is a diagram showing variations of the space pattern of an island area or a peninsular area formed on the aluminum sheet of the tablet PTP package according to the second embodiment of the invention. The basic form of (a) in FIG. 4 is a first variation of the space pattern forming an island area for linear polarization (unidirectional polarization) with the wavelength of $\lambda/2$. A first modification shown in (b) of FIG. 4 is a second variation of the space pattern forming a U-shaped peninsular area linear polarization (unidirectional polarization) with the wavelength of $\lambda/4$.

With the peninsular pattern as the first modification shown in (b) of FIG. 4, for example, the "RFID tag" can be formed one half in size of the basic form shown in (a) of FIG. 4. Thus, the "RFID tag" can be mounted on a still smaller PTP package and the application range of the "RFID tag" is widened.

Figure 13A:
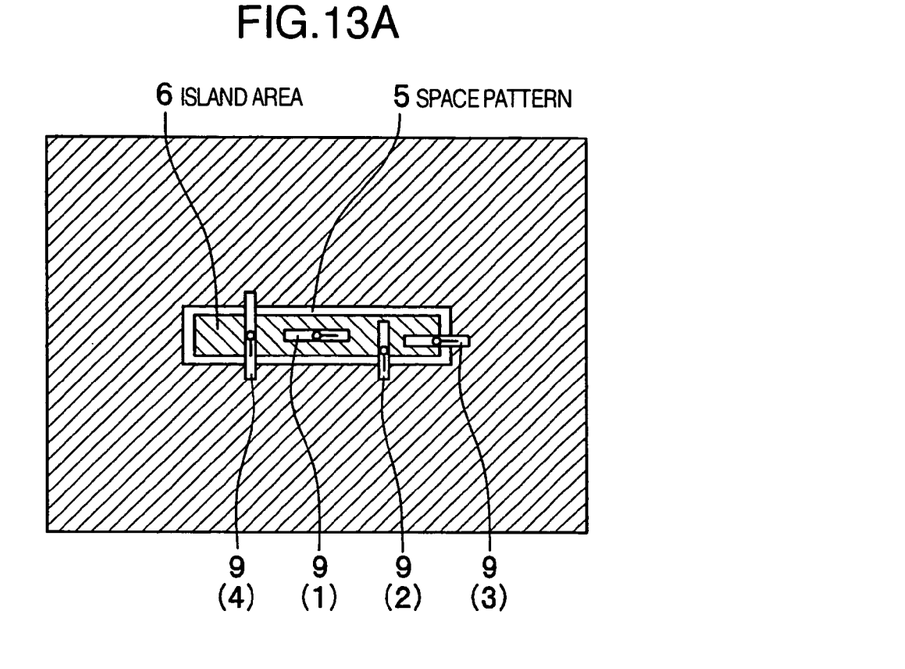
FIGS. 13A and 13B are diagrams showing the relative positions of the space pattern formed on a metal foil and the small inlet.

The basic form of (a) in FIG. 4 has four patterns (1) to (4) of arrangement of the small radio IC inlet as shown in FIG. 13A, including the pattern (1) arranged on the island area 6, the pattern (2) arranged across the space pattern on the long side of the island area 6, the pattern (3) arranged across the space pattern on the short side of the island area 6, and the pattern (4) arranged across the island area 6 (FIG. 13A). Also for second and fourth modifications shown in (c) and (e) of FIG. 4, the small radio IC inlet can be arranged in any of the four patterns described above.

Figure 13B:
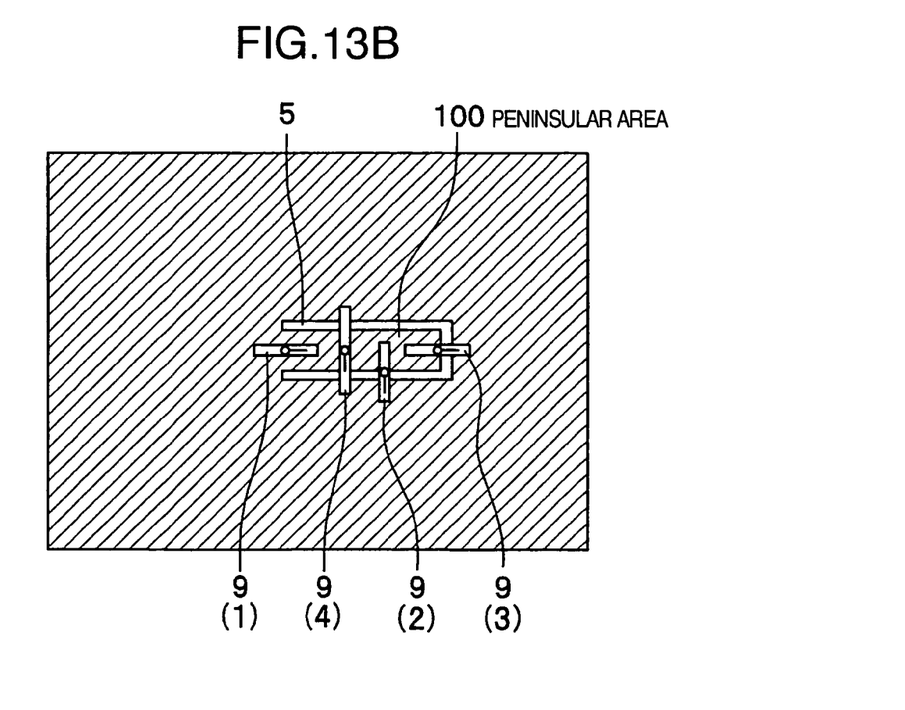

As for the first modification shown in (b) of FIG. 4, on the other hand, the small radio IC inlet 9 can be arranged in any of four patterns (1) to (4) shown in FIG. 13B. Specifically, they include the pattern (1) arranged in the peninsular area 100, the pattern (2) arranged across the space pattern 6 on the long side of the peninsular area 100, the pattern (3) arranged across the space pattern 6 on the short side of the peninsular area 100, and the pattern (4) arranged across the peninsular area 100. Also for the second and fourth modifications shown in (c) and (e) of FIG. 4, the small radio IC inlet 9 can be arranged in any of the four patterns described above.

As described above, in the case where the island area 6 or the peninsular area 100 is used as an antenna, the small radio IC inlet 9 can be arranged in any of the four patterns. This increases the freedom of mounting the small radio IC inlet 9. Also, in (a) and (b) of FIG. 4, the small radio IC inlet 9 can be arranged in the direction parallel to the long or short side of the island area 6 or the peninsular area 100, and therefore the size of the short side of the "RFID tag" can be minimized. In other words, the small radio IC inlet 9 can be reduced in size.

The second modification shown in (c) of FIG. 4 derives from the basic form of (a) of FIG. 4, and represents a third variation of the space pattern forming the island area for bidirectional polarization (i.e. in two directions of X and Y axes) with the wavelength of $\lambda/2$. Specifically, the antenna having the shape of this variation can be used in two polarization planes in different directions of X and Y axes. In the case shown, the horizontal island area contributes to horizontal polarization, and the vertical island area to vertical polarization. The third modification shown in (d) of FIG. 4 derives from the first modification shown in (b) of FIG. 4 and represents a fourth variation of the space pattern forming a peninsular area for bidirectional polarization (polarized in two directions of X and Y axes) with the wavelength of $\lambda/4$.

In the second and third modifications, the "RFID tag" can be read by polarization in two directions. Therefore, the information of the "RFID tag" can be read without matching the reader-writer carrying an antenna of linear polarization (unidirectional polarization) with each polarization plane of the "RFID tag". Examples of the linear polarization antenna include a dipole antenna, a patch antenna and a small dielectric antenna. As a result, the user can conduct the read operation without being conscious of the direction in which the "RFID tag" is read, and therefore the working efficiency is improved.

The fourth modification shown in (e) of FIG. 4 derives from the basic form of (a) of FIG. 4 and represents a fifth variation of the space pattern formed in the shape of U by bending the ends of the island shown in (a) of FIG. 4.

In the fourth modification, as compared with the basic form shown in (a) of FIG. 4, the "RFID tag" can be reduced in size. As in the second and third modifications shown in (c) and (d) of FIG. 4, the "RFID tag" can be read by bidirectional polarization, and therefore the information of the "RFID tag" can be read more easily. Further, a margin (package margin) is usefully created in the package space of the "RFID tag".

THIRD EMBODIMENT

Figure 5:
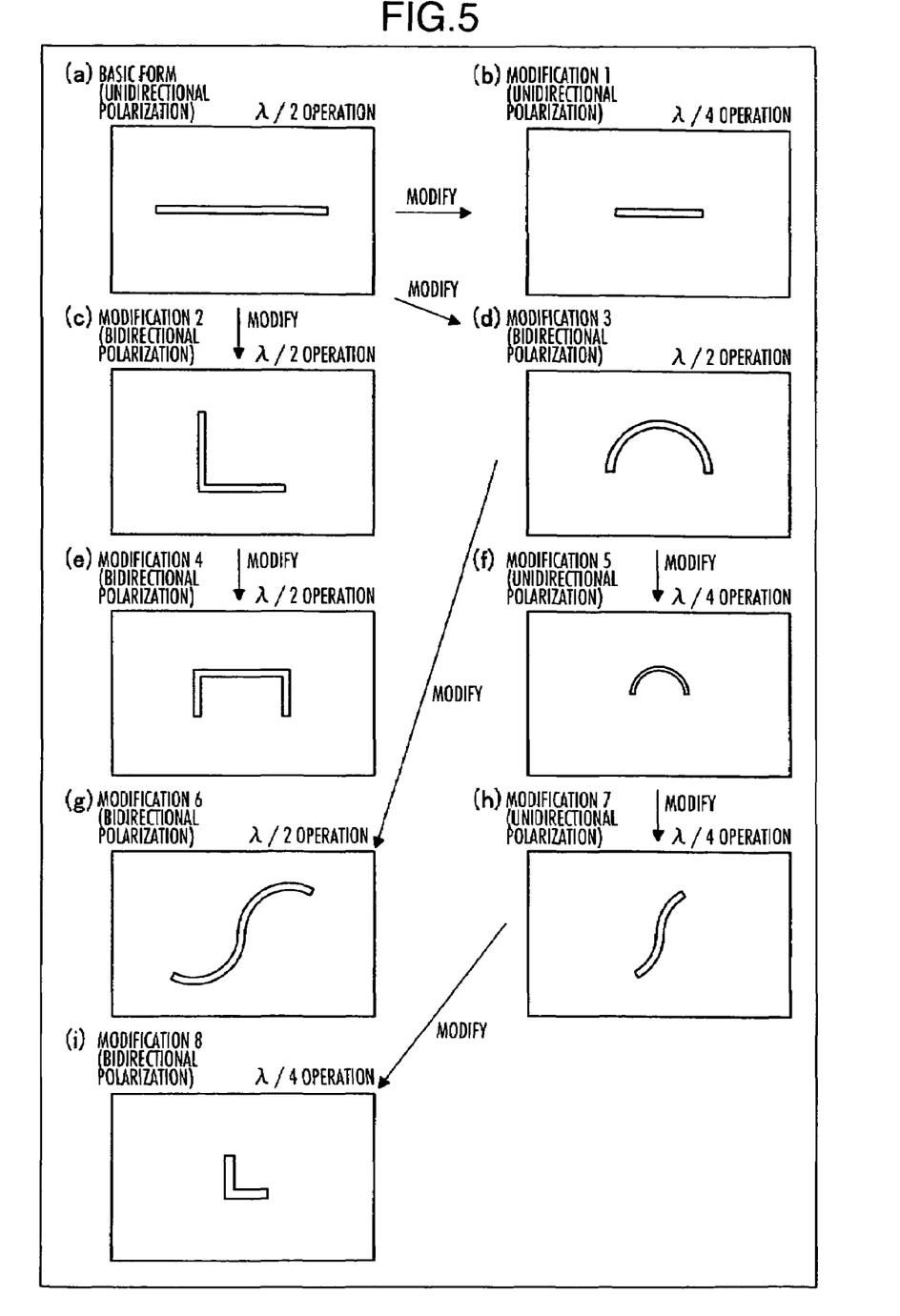
FIG. 5 is a diagram showing variations of the slotted space pattern formed in the wide metal foil area according to a third embodiment of the invention.

As a third embodiment, several variations in which a slotted space pattern is formed in a wide metal foil area are explained. FIG. 5 is a diagram showing variations in which a slotted space pattern is formed in a wide metal foil area according to the third embodiment of the invention. In (a) of FIG. 5, a basic form is shown in which a linear slotted space pattern of $\lambda/2$ long is formed in the metal foil area for linear polarization with the wavelength of $\lambda/2$. The first modification shown in (b) of FIG. 5 represents a modification of the basic form shown in (a) of FIG. 5 and represents a state in which the linear slotted space pattern $\lambda/4$ long is formed in the metal foil area for linear polarization with the wavelength of $\lambda/4$.

The second modification shown in (c) of FIG. 5 derives from the basic form shown in (a) of FIG. 5, and represents the state in which a hook-shaped slotted space pattern is formed in the metal foil area from a linear pattern $\lambda/2$ long for bidirectional polarization with the wavelength of $\lambda/2$. In the read operation with this bidirectional polarization, the information of the "RFID tag" attached on an article can be read with a reader-writer fixed without being moved toward the side of the article carrying the "RFID tag" each time. The third modification shown in (d) of FIG. 5 derives from the basic form shown in (a) of FIG. 5 and represents the state in which a semicircular slotted space pattern is formed in the metal foil area from a linear pattern $\lambda/2$ long for bidirectional polarization with the wavelength of $\lambda/2$. The fourth modification shown in (e) of FIG. 5 derives from the second modification shown in (c) of FIG. 5 and represents the state in which a U-shaped slotted space pattern is formed in the metal foil area from a linear pattern $\lambda/2$ long for bidirectional polarization with the wavelength of $\lambda/2$. By changing the length of the U-shaped slot along X and Y axes, the direction of bidirectional polarization can be adjusted toward X or Y direction. The fifth modification shown in (f) of FIG. 5 derives from the third modification shown in (d) of FIG. 5 and represents the state in which a semicircular slotted space pattern is formed in the metal foil area from a linear pattern $\lambda/4$ long for linear polarization with the wavelength of $\lambda/4$.

The sixth modification shown in (g) of FIG. 5 derives from the third modification shown in (d) of FIG. 5 and represents the state in which an S-shaped slotted space pattern is formed in the metal foil area from a linear pattern $\lambda/2$ long for bidirectional polarization with the wavelength of $\lambda/2$. The seventh modification shown in (h) of FIG. 5 derives from the fifth modification shown in (f) of FIG. 5 and represents the state in which an S-shaped slotted space pattern is formed in the metal foil area from a linear pattern $\lambda/4$ long for linear polarization with the wavelength of $\lambda/4$. The eighth modification shown in (i) of FIG. 5 derives from the seventh modification shown in (h) of FIG. 5 and represents the state in which a hook-shaped slotted space pattern is formed in the metal foil area from a linear pattern $\lambda/4$ long for bidirectional polarization with the wavelength of $\lambda/4$.

FOURTH EMBODIMENT

In the fourth embodiment of the invention, a method of arranging the small radio IC inlet in the space pattern is explained. In the case where the space pattern forms an island area, as shown in FIG. 1, the small radio IC inlet is arranged along the length of the antenna area formed by the island area. In the case where the slotted space pattern is formed as shown in FIG. 5, however, the small radio IC inlet is arranged orthogonally to the space pattern.

Figure 6A:
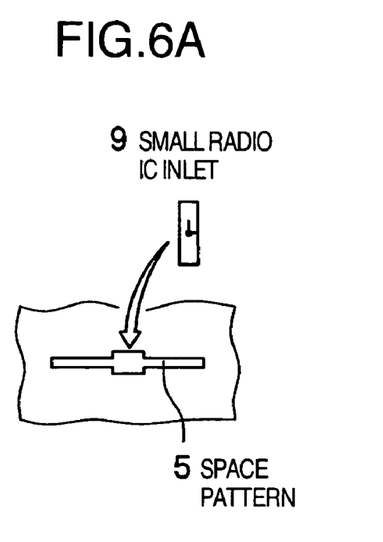
FIGS. 6A and 6B are schematic diagrams showing the manner in which a small radio IC inlet is arranged orthogonally to the slotted space pattern formed according to a fourth embodiment of the invention.
Figure 6B:
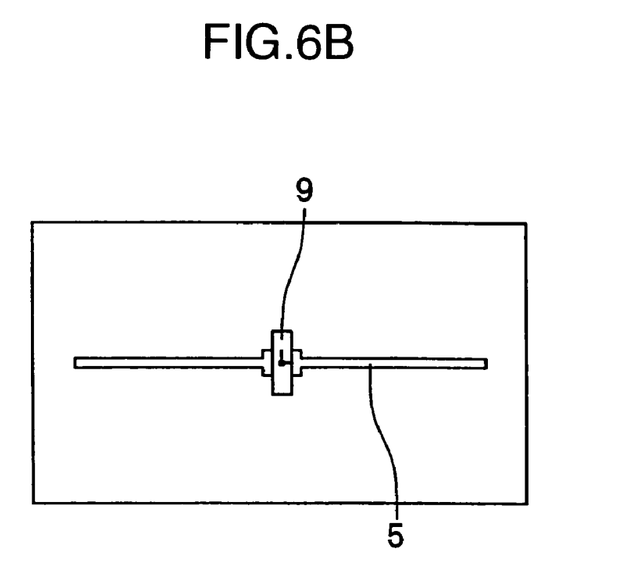

FIGS. 6A and 6B are schematic diagrams showing the manner in which the small radio IC inlet is arranged orthogonally to the slotted space pattern. In FIG. 6A, the slot length of the slotted space pattern 5 is not less than $\lambda/4$ and the slot width is not less than 0.1 mm. In order to provide a margin of arrangement of the small radio IC inlet, the slot width of the portion of the space pattern 5 where the small radio IC inlet is arranged is increased. Specifically, in order to reduce the mounting accuracy of the small radio IC inlet 9 on the space pattern 5, the slot width of the portion where the small ratio IC inlet 9 is mounted is increased. Thus, the small radio IC inlet 9 is arranged orthogonally to the portion of the space pattern 5 having a large width (FIG. 6B).

In FIGS. 6A and 6B, the small radio IC inlet 9 is arranged at the central portion on the space pattern 5. Nevertheless, the mounting position of the small radio IC inlet is not necessarily limited to the central portion of the space pattern 5.

The mounting margin of the small radio IC inlet 9 can be increased, as in the case of FIG. 6, also by inserting an insulating member between the small radio IC inlet 9 and a metal member forming the space pattern 5 and securing a wide interval between the small radio IC inlet 9 and the metal member forming the space pattern 5.

This effect is exhibited by an insulating member at least 0.05 mm thick. In the case where the adhesive attached on a board to fix the small radio IC inlet 9 is increased to 0.3 mm thick, for example, the mounting margin of the small radio IC inlet 9 can be easily increased.

The simultaneous use of the aforementioned two methods, i.e. a method of arranging the small radio IC inlet 9 as shown in FIG. 6 and a method of inserting the metal member can also produce the effect of increasing the mounting margin of the small radio IC inlet 9.

FIFTH EMBODIMENT

Figure 7:
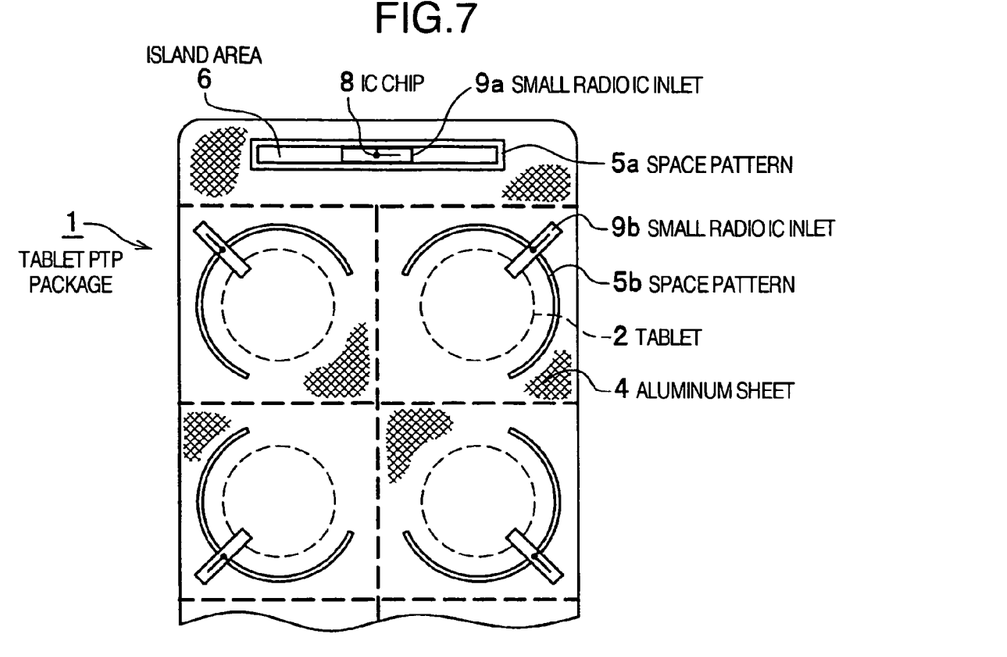
FIG. 7 is a diagram showing an arrangement of a space pattern for overall management of the tablet PTP package and individual management of tablets shown in FIG. 1 according to a fifth embodiment of the invention.

In the fifth embodiment of the invention, the arrangement of the space pattern for overall management of the tablet PTP package and individual management of the tablets shown in FIG. 1 is explained. FIG. 7 is a diagram showing the arrangement of the space pattern for overall management of the tablet PTP package and individual management of the tablets in FIG. 1 according to the fifth embodiment of the invention.

As shown in FIG. 7, a space pattern 5a is formed on an aluminum sheet 4 of a tablet PTP package 1 thereby to form an elongate island area 6. This elongate island area 6 constitutes an antenna area, along the length of which a small radio IC inlet 9a is mounted. As a result, the small radio IC inlet 9a functions as a "RFID tag" having a comparatively large island area 6 (i.e. antenna area), and therefore a radio wave having a high radio strength can be radiated from the small radio IC inlet 9a. The radio wave radiated from the "RFID tag" including the space pattern 5a and the small radio IC inlet 9a having this configuration is read by a reader-writer thereby to perform the overall management of the tablet PTP package 1.

On the other hand, the aluminum sheet 4 is formed with an arcuate space pattern 5b having the length of $\lambda/2$ along the outer periphery of each tablet 2, and the small radio IC inlet 9b is arranged orthogonally to each arcuate space pattern 5b. Any tablet 2 remaining in the tablet PTP package without being used, therefore, can be detected by the corresponding "RFID tag" including the space pattern 5b and the small radio IC inlet 9b. Once any tablet 2 is retrieved by breaking the aluminum sheet 4, on the other hand, the portion of the aluminum sheet 4 in the neighborhood of the corresponding space pattern 5b is broken, and therefore the corresponding "RFID tag" including the space pattern 5b and the small radio IC inlet 9b ceases to radiate the radio wave. As a result, it can be confirmed whether each tablet in the tablet PTP package has been taken or not.

SIXTH EMBODIMENT

Figure 8:
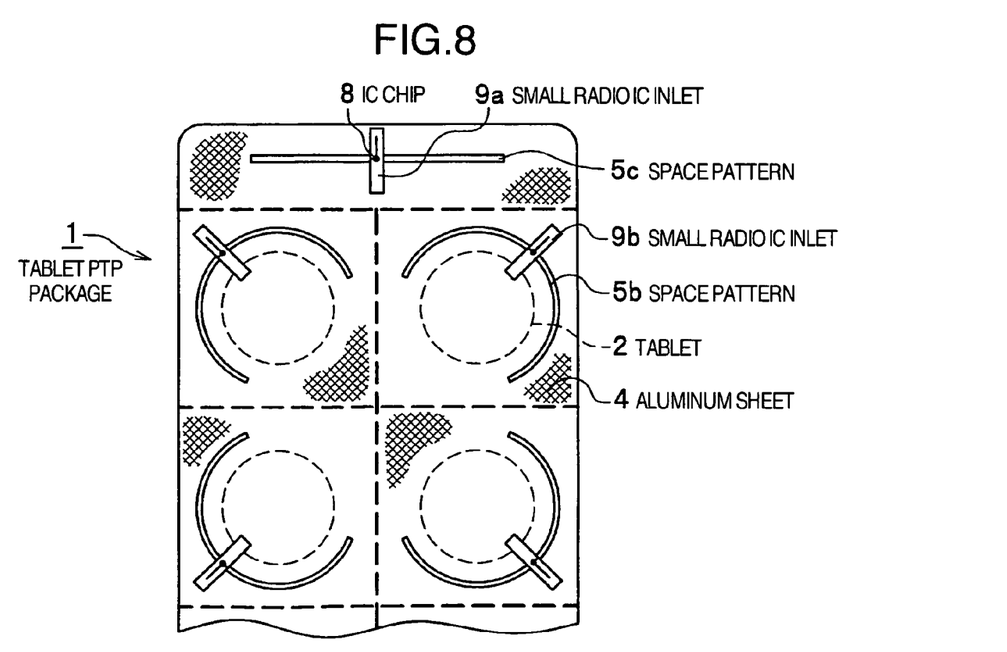
FIG. 8 is a diagram showing another arrangement of the space pattern for overall management of the tablet PTP package and individual management of tablets according to a sixth embodiment of the invention.

As a sixth embodiment of the invention, another method of arranging the space pattern for overall management of the tablet PTP package and individual management of each tablet is explained. FIG. 8 is a diagram showing another arrangement of the space pattern for overall management of the tablet PTP package and individual management of each tablet according to the sixth embodiment of the invention. As shown in FIG. 8, a linear space pattern (i.e. slot) 5c having a length of $\lambda/2$, for example, is formed in an aluminum sheet 4 of a tablet PTP package 1, and a small radio IC inlet 9a is mounted orthogonally to the space pattern 5c. Specifically, the "RFID tag" according to the invention can be configured by arranging the small radio IC inlet 9a orthogonally to the linear space pattern 5c as shown in FIG. 8 without forming an island area in the space pattern shown in FIG. 1. In the process, the space pattern 5c matches the impedance between the IC chip 8 mounted on the small radio IC inlet 9a and the antenna formed by the aluminum sheet 4, and therefore a radio wave high in strength and high directivity can be radiated from the small radio IC inlet 9a. The overall management of the tablet PTP package 1 made possible by a "RFID tag" including the space pattern 5c and the small radio IC inlet 9a having this configuration.

The aluminum sheet 4, on the other hand, is formed with an arcuate space pattern 5b having a length of λ/2 along the outer periphery of each tablet 2, and the small radio IC inlet 9a is arranged orthogonally to the arcuate space pattern 5b.

In the case where one small "RFID tag" 9b is mounted for each tablet 2 in this manner, the following effect is produced. Specifically, the patient trying to use the tablet 2 in the PTP package can confirm the information (the material of the production lot, the processing steps, the distribution route, etc.) on the tablet 2 by reading it from the small "RFID tag" 9b corresponding to the particular tablet 2 using the reader-writer. Then, the patient can take the tablets (medicines) in the PTP package safely.

Alternatively, before the patient takes a tablet, the ID information (i.e. ID for identifying each small "RFID tag") of the corresponding small "RFID tag" 9b mounted on the particular tablet may be received by a computer system not shown so that the ID information is managed on a data base (not shown). Specifically, the information (date and hour the tablet is taken by the patient, amount taken and the name of the tablet, etc.) on the patient who has taken the tablet 2 carrying the small "RFID tag" 9b designated in the ID information is also managed on the data base. By doing so, the present and past situations in which the patient takes and has taken the tablets can be managed.

In the case where a highly hygroscopic medicine is used, for example, each PTP package 1 may be contained and packed in a moisture proof bag having a stack structure such as PET/PE/AL/PE. In such a case, the small "RFID tag" is mounted also on the moisture proof bag. By doing so, as in the aforementioned case, the computer system not shown receives the ID information (ID of the small "RFID tag" mounted) of the small "RFID tag" with the radio IC inlet 9a mounted on the aluminum sheet 4 of the PTP package 1 and the ID information (ID of the small "RFID tag" mounted) of the small "RFID tag" with the radio IC inlet 9b mounted on the particular moisture proof bag, and these information can be managed on the data base as mutually corresponding information. Without retrieving the medicine from the PTP package 1, therefore, the particular medicine can be finally identified from the combined information of the preset two "RFID tag"s. This is also true in the case where a plurality of the PTP packages 1 are contained and packaged in one moisture proof bag.

Further, the small "RFID tag" may be mounted on, for example, the document (written instruction) attached to the medicine. A computer system not shown thus receives also the IC information of the small "RFID tag" mounted on the attached document and can manage it on the data base. In this way, the document management of the attached document is made possible.

The embodiment described above deals with the PTP package, to which the invention is not limited and applicable also to the bag-type strip package or the blood transfusion bag.

SEVENTH EMBODIMENT

Figure 9:
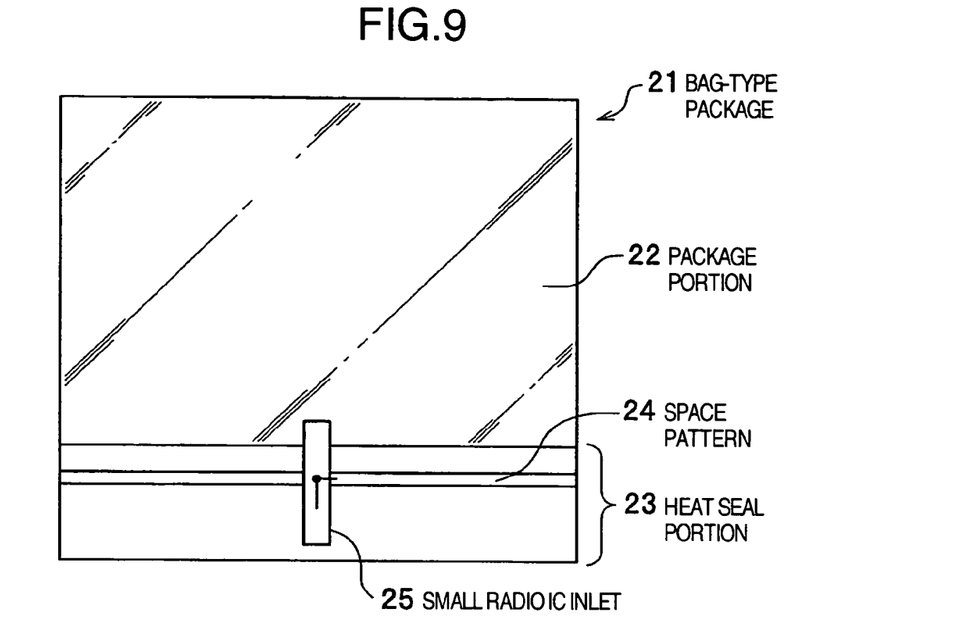
FIG. 9 is a top plan view of a bag-type package in which the space pattern formed in the aluminum sealed portion of a resin package has an open end according to a seventh embodiment of the invention.

As a seventh embodiment, an explanation is made about a case in which each bag of a powdered medicine or frozen food is managed. FIG. 9 is a plan view showing a bag-type package such as a strip package for the medicine or a retort pouch for foods according to the seventh embodiment of the invention, in which the space pattern formed on the thermally compressed portion (heat seal portion) of a resin package using a package film constituted of a lamination of an aluminum foil or an aluminum vapor-deposition film. As shown in FIG. 9, a powdered medicine or the like is contained in the package portion 22 of the bag-type package 21 and sealed by a heat seal portion 23. A space pattern 24 is formed over the whole width of the heat seal portion 24 of the aluminum sheet. A small radio IC inlet 25 is arranged orthogonally to the space pattern 24 at about the central part thereof. Although the space pattern 24 has an open end, the aluminum sheet of the heat seal portion 23 functions as an antenna and therefore the medicine in the package portion 22 can be managed.

Even in the case where the space pattern 24 is slightly zigzagged, the aluminum sheet can function as an antenna.

Specifically, before opening the bag-type package 21 configured as shown in FIG. 9, the information on the powdered medicine or the like sealed in the bag-type package 21 can be known by the "RFID tag" with the space pattern 24 and the small radio IC inlet 25. Once the bag-type package 21 is opened by cutting the space pattern 24 with fingers or scissors, the small radio IC inlet 25 loses the function of transmitting a radio wave, and therefore it is possible to detect whether the patient has taken the medicine or not.

Further, in the case where a plurality of bag-type packages 21 such as strip packages (containing a powdered medicine) are connected to each other, the bag-type packages 21 are separated along the space pattern 24 and the antenna of the small "RFID tag" is destroyed when the medicine is taken. The time when the communication with the antenna fails due to the antenna destruction, for example, can be managed on the data base of the computer system as the time point when the patient takes the medicine. In this way, the data base user can grasp the time point when the patient has taken the powdered medicine or the like in the bag-type package. As another alternative, the ID information of the tag antenna destroyed and the information on the contents (such as the amount of the powdered medicine) of the bag-type package are related to each other in advance on the data base, so that the data base user can grasp also the amount of the medicine that the patient has taken.

Figure 10:
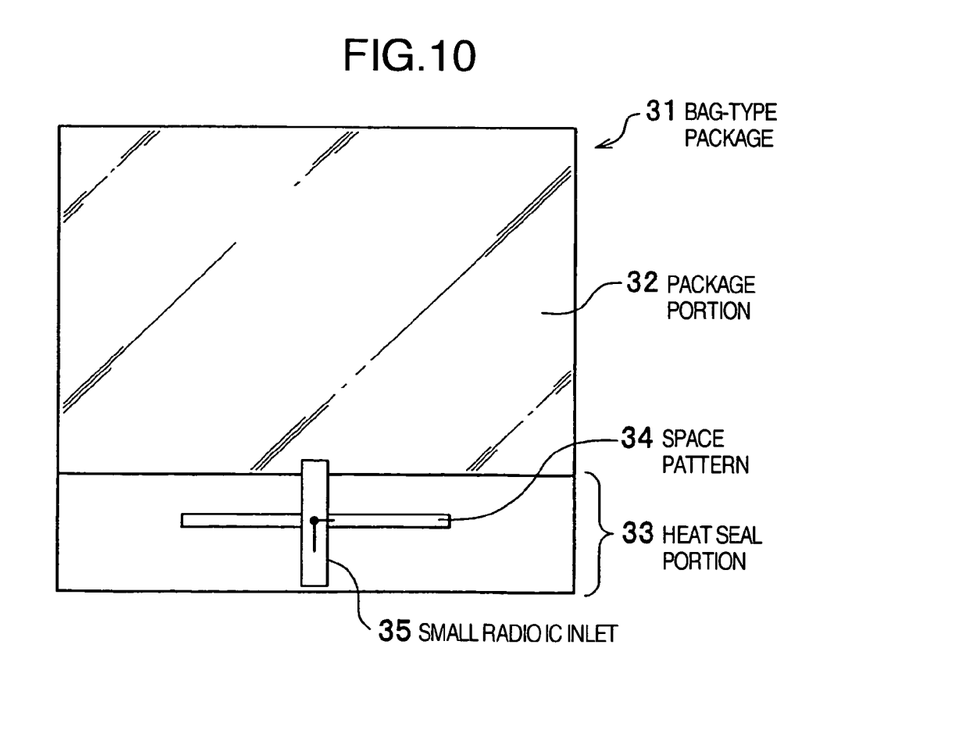
FIG. 10 is a top plan view of a bag-type package in which the space pattern is formed in the thermally compressed portion sealing the package portion of the aluminum sheet according to the seventh embodiment of the invention.

FIG. 10 is a plan view of a bag-type package with a space pattern 34 formed on the thermally compressed portion (heat seal portion) sealing the package portion of an aluminum sheet according to the seventh embodiment of the invention. In FIG. 10, a powdered medicine or the like is contained in the package portion 32 of an aluminum sheet and sealed by the thermally compressed portion (heat seal portion) 33 of the aluminum sheet. The space pattern 34 is formed at about the central portion of the thermally compressed portion (heat seal portion) 33 sealing the package portion 32 of the aluminum sheet. Further, the small radio IC inlet 35 is arranged across the central portion of the space pattern 34.

An adhesive about 0.05 mm to 1.0 mm thick is attached on the reverse surface of the small radio IC inlet 35, and therefore the small radio IC inlet 35 is firmly bonded without being raised substantially from the aluminum sheet. The small radio IC inlet 35 with a resin seal or the like attached on the upper surface thereof may alternatively be fixed on the aluminum sheet. Further, the mounting margin of the small radio IC inlet 35 can be increased by embossing the surface of the mounting portion thereof.

The bag-type package 31 configured as shown in FIG. 10 is opened in such a manner as to cut off the space pattern 34 with fingertips or scissors. As long as the bag-type package 31 remains closed, the information on the powdered medicine (name of the medicine, etc.) contained in the bag-type package 31 can be read by the "RFID tag" including the small radio IC inlet 35 and the space pattern 34. Once the bag-type package 31 is opened, however, the small radio IC inlet 35 and the space pattern 34 are destroyed and therefore no information can be read. In this way, the opened and closed states of the aluminum package can be managed.

Further, in the case where a plurality of strip packages (containing a powdered medicine) or the like bag-type packages are connected, the bag-type packages, when used, are separated along the space pattern 34 and the antenna of the "RFID tag" is destroyed. As in the case of FIG. 9, therefore, the data base user can grasp the time when the patient took the medicine or the amount of the medicine taken by the patient using the data base.

EIGHTH EMBODIMENT

Figure 11:
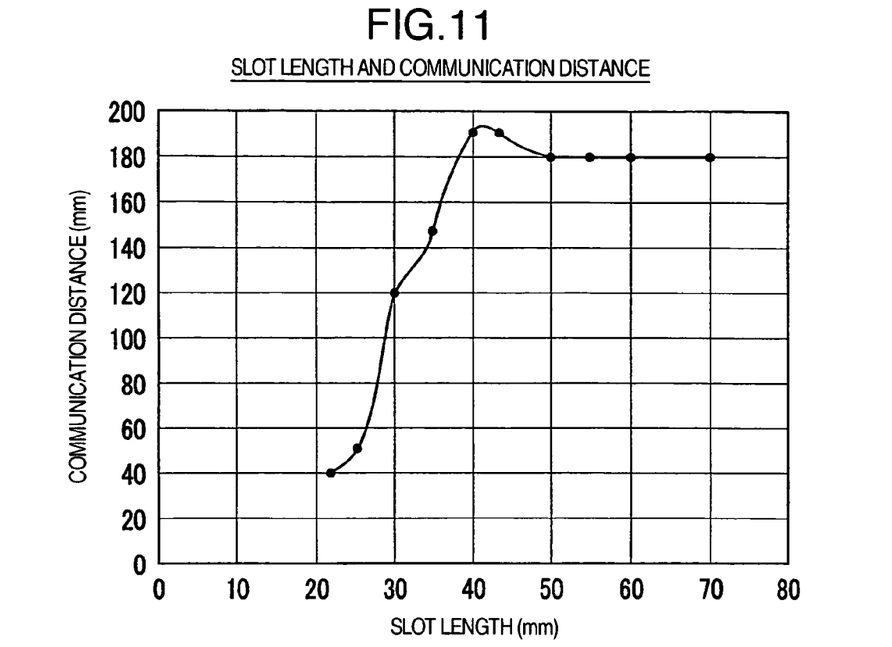
FIG. 11 is a characteristic diagram based on experiments showing the relation between the length of the slot formed by the space pattern and the communication distance according to the invention.

In the eighth embodiment, a study based on experimental data is made about the manner in which the communication distance changes with the length of the slot formed by the space pattern and the position at which the small radio IC inlet is mounted on the slot. FIG. 11 is a characteristic diagram based on the result of experiments conducted according to the invention, and shows the relation between the communication distance and the length of the slot formed by the space pattern. In FIG. 11, the abscissa represents the slot length in mm and the ordinate the communication distance.

As understood from FIG. 11, the communication distance is substantially constant at 180 mm for the slot length of not less than 50 mm (i.e. $\lambda/2$). For the slot length of between 50 mm and 40 mm, on the other hand, the communication distance is slightly longer than 180 mm. In the case where the slot length is reduced to less than 40 mm, the communication distance sharply decreases, and for the slot length of 25 mm ($\lambda/4$), becomes as short as 40 mm. This indicates that the slot length (i.e. the length of the space pattern) of the "RFID tag" according to the invention is most desirably about $\lambda/2$. With the slot length about 20% more or less than $\lambda/2$, however, the communication distance substantially remains unchanged. In this way, the margin of the slot length is very large, and therefore, in the case where the "RFID tag" according to the invention at the normal quality level is mass produced, a sufficiently high yield can be secured.

Figure 12:
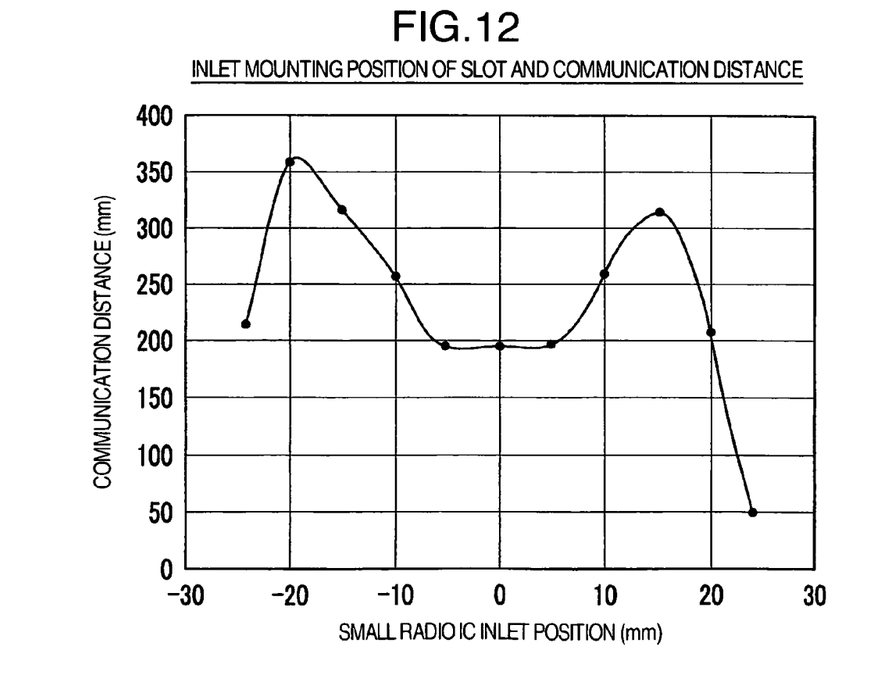
FIG. 12 is a characteristic diagram based on experiments showing the relation between the mounting position of a small radio IC inlet on the slot formed by the space pattern and the communication distance according to the invention.

FIG. 12 is a characteristic diagram based on the experimental result according to the invention and shows the relation between the mounting position of the small radio IC inlet on the slot formed by the space pattern and the communication distance. In FIG. 12, the abscissa represents the mounting position in mm of the small radio IC inlet and the ordinate the communication distance. Referring to FIG. 10 showing the mounting position of the small radio IC inlet, assume that the longitudinal center of the slot at which the small radio IC inlet is mounted is the mounting position of 0 mm, and that the mounting position of the small radio IC inlet, if displaced rightward of the space pattern in FIG. 10, is changed positively, and vice versa.

As shown in FIG. 12, as long as the mounting position of the small radio IC inlet remains 0 mm (i.e. in the case where the small radio IC inlet is mounted at the longitudinal center of the slot), the communication distance is about 200 mm. According as the mounting position of the small radio IC inlet changes rightward of the slot (i.e. according as the mounting position changes positively), the communication distance is correspondingly lengthened and then reduced. According as the mounting position of the small radio IC inlet changes leftward of slot (i.e. according as the mounting position changes negatively), on the other hand, the communication distance is also correspondingly lengthened and then reduced. In the process, the change in communication distance is substantially symmetric between the rightward (positive) and the leftward (negative) change of the mounting position of the small radio IC inlet with respect to the slot. As understood from FIG. 12, even in the case where the mounting position of the small radio IC inlet is displaced by about ±20 mm, the communication distance of not less than 200 mm is secured. This indicates that even in the case where the mounting position of the small radio IC inlet is displaced considerably from the slot center, the communication distance is not reduced, and therefore the margin of the mounting position of the small radio IC inlet is very high.

The result of the experiments described above shows that both the margin of the slot length and the margin of the mounting position of the small radio IC inlet are very high, and therefore a sufficiently high yield can be secured even in the case where the "RFID tag" according to the invention is mass produced at the normal product quality level.

[Modifications of Island and Peninsular Antennas]

Next, modifications of the island and peninsular antennas are explained with reference to FIGS. 14A to 14C.

Figure 14A:
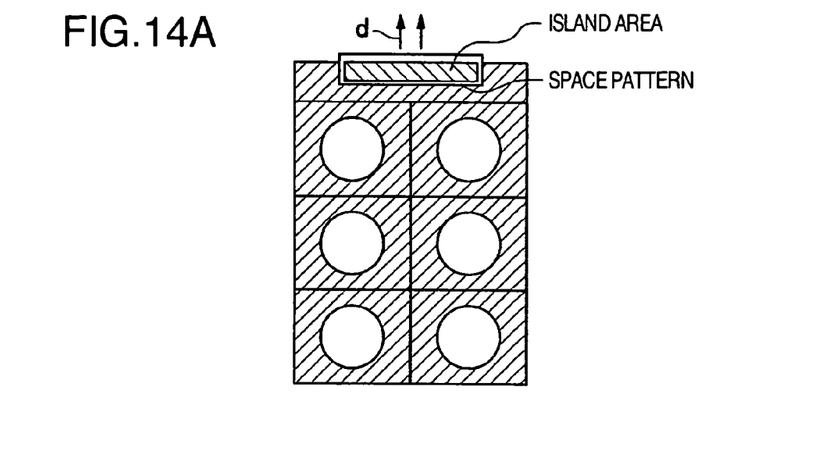
FIGS. 14A and 14B are diagrams showing modifications of the island and peninsular antennas.
Figure 14B:
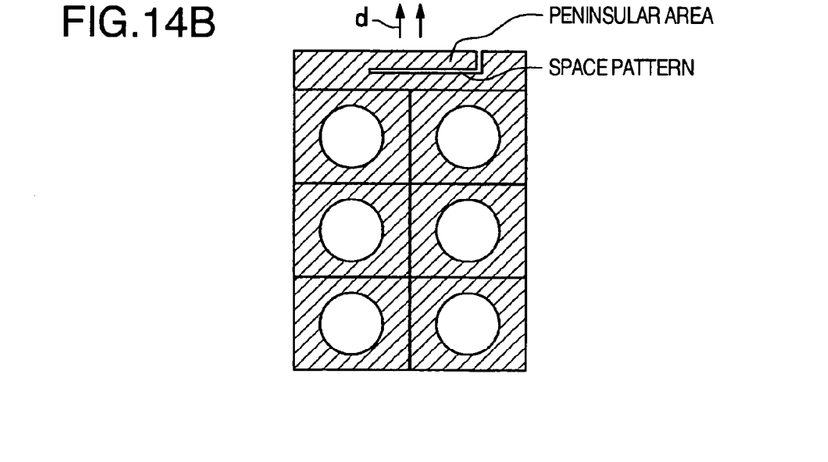

In the island antenna shown in FIG. 14A and the peninsular antenna shown in FIG. 14B, one side of the space pattern is located at the end of the PTP package. This configuration makes it possible to form a "RFID tag" in a very elongate area. In the case where the island area shown in FIG. 14A has a width of 2.0 mm and the width of the space pattern is 0.5 mm, for example, the "RFID tag" can be mounted on the PTP package as long as an area of 2.5 mm (2.0+0.5 mm) is secured on the upper surface of the PTP package. Also, as compared with the basic form of island pattern (FIG. 4A) and peninsular pattern (FIG. 4B), the radiation strength in the radiation direction d shown in FIGS. 14A, 14B is increased. Incidentally, the mounting method of the small radio IC inlet is explained already (FIGS. 13A, 13B).

Figure 14C:
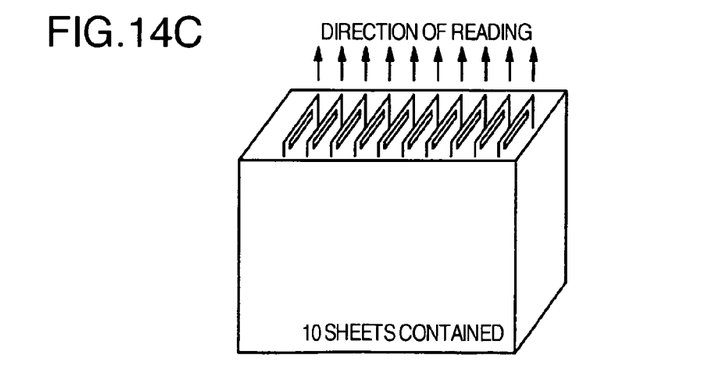
FIG. 14C is a diagram showing direction of reading RFID tags in the case where a plurality of the PTP packages are packed in a box.

In the case where a plurality of the PTP packages are packed in a box as shown in FIG. 14C, the readability from a single surface (upper surface of the box, for example) is improved.

<<Conclusion>>

As described above, the conventional antenna having a structure called the slot antenna is required to have a feeding point at a specified position of the slot forming portion where the impedance matching is possible, and therefore has a very small margin of the IC chip mounting position. In the "RFID tag" according to the invention, on the other hand, an impedance matching portion is formed in advance as a small radio IC inlet on the small antenna on which the IC chip is mounted, and the small radio IC inlet alone can perform the radio wave transmitting operation. Also, the "RFID tag" is formed by mounting the small radio IC inlet with the IC chip on the island area or the slot formed by the space pattern. With the "RFID tag" having this configuration, a superior antenna directivity with a high radio wave strength can be achieved even in the case where the mounting position of the small radio IC inlet is somewhat displaced. In other words, the change in communication distance is small with the change in the slot mounting position of the small radio IC inlet, and therefore the margin of the mounting position on the slot of the small radio IC inlet very high.

Also, in the "RFID tag" according to the invention, a space pattern is formed at the desired position on a metal film formed over the whole surface of at least one side of a package, and a small radio IC inlet with an IC chip and a small antenna having an impedance matching circuit is mounted on a slot formed by the space pattern through a resin material of PVC, PE, PP or PC on the other surface of the package to which a metal film is attached. At the same time, the small radio IC inlet is mounted orthogonally to the space pattern.

The support member of the small antenna having the IC chip mounted thereon has the thickness of not less than 0.02 mm, and in the case where the thickness of the support member is less than 0.02 mm, a spacer to compensate for the thickness is interposed under the small radio IC inlet. The spacer is formed of a resin material such as PE, PP, PET or PVC or a foamed version of any of these resin materials. Other material candidates include a rubber material, a foamed rubber material or paper.

The antenna formed by the space pattern may be in the shape of island, peninsula or slot. Further, the antenna may assume the form of a linear or L-, S- or C-shaped slot. The small antenna making up the small radio IC inlet includes an impedance matching circuit (i.e. a slit). Further, the small radio IC inlet is mounted on an island area or a slot through the support member of the resin material. In the process, the small radio IC inlet with an adhesive attached to the bottom thereof is used. The adhesive acts also as a spacer.

The "RFID tag" according to the invention is manufactured in one of the two methods described below.

(1) In the PTP package, the aluminum sheet and the PVC are collectively pressed in a die thereby to form an island area or a slot of the space pattern. The small radio IC inlet is mounted on the island area or the slot, as the case may be.

(2) A space pattern is formed in advance on the aluminum sheet of a PTP package, and the resulting aluminum sheet is used to form the PTP package. The small radio IC inlet is mounted on the island area or the slot formed by the space pattern.

The "RFID tag" according to the invention can be mounted on various electric devices for information management. A linear or S- or C-shaped space pattern is formed, for example, on the measuring instrument, the control equipment, the equipment panel such as WS (Work Station), the display unit or the meter panel surface, and a small radio IC inlet prepared in advance is mounted on the island area or slot formed by the space pattern. In this case, the resin such as PE, PET or PP or a foamed version thereof is interposed between the small radio IC inlet and a metal panel.

The "RFID tag" according to the invention can be mounted on the package sealed with aluminum. The "RFID tag" according to the invention can be mounted on, for example, the aluminum-sealed package widely used for the processed foods and daily goods. In the process, an island area or a slot is formed by the space pattern in the thermally compressed portion at the package end and the small radio IC inlet is mounted. As an alternative, the island area or slot is formed by the space pattern in advance on the aluminum-sealed portion in the package, and the small radio IC inlet is mounted on this island area or slot.

As another alternative, a space pattern is formed in the GND pattern of the PCB board forming an electrical circuit, and the "RFID tag" carrying the IC chip and the small antenna is mounted on the space pattern using an adhesive or a pressure sensitive adhesive. As still another alternative, an IC chip is mounted by forming a pattern of the small radio IC inlet on the PCB board. Specifically, the "RFID tag" according to the invention has an impedance matching circuit on the small antenna side, and therefore the resulting large design allowance of the space pattern formed on the PCB board makes it possible to fabricate the pattern of the small radio IC inlet roughly (with low accuracy).

Also, the "RFID tag" according to the invention can be mounted on a gas cylinder. Specifically, a cylinder sleeve or a metal plate tag (such as an iron plate or a name plate) is mounted to form a mounting portion on which a slit pattern is formed and the small radio IC inlet is mounted. In the process, a resin-molded tag or like which can be inserted into the space pattern is desirably used to increase the mounting strength.

Further, the "RFID tag" according to the invention can be utilized for management of the semiconductor photomask. Specifically, a space pattern is formed on a Cr membrane constituting a photomask material at the end of the photomask used for semiconductor fabrication. A small radio IC inlet including a small antenna with an IC chip is mounted on the space pattern using an adhesive or a pressure sensitive adhesive. The space pattern is formed by etching at the mask end simultaneously with the semiconductor pattern at the time of photomask fabrication.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A RFID (radio frequency identification) tag for transmitting information recorded in an IC chip by radio communication, comprising:
    an inlet including the IC chip mounted on a small antenna formed with a slit for impedance matching; and
    a second antenna implemented by a space pattern formed in a metal foil, the space pattern including an aperture through the metal foil,
    wherein as a result of forming the space pattern including the aperture, a protrusion is formed on a resin sheet, and
    wherein the inlet is mounted on a surface of the second antenna, and the small antenna and the second antenna are electrostatically coupled to each other.

2. The RFID tag according to claim 1, wherein the space pattern forms the second antenna with an island area isolated from remaining area of the metal foil.

3. The RFID tag according to claim 2, wherein the second antenna formed by the island area has an electrical length of $\lambda/2$, where $\lambda$ is the wavelength of the radio wave radiated from the small antenna.

4. The RFID tag according to claim 1,
    wherein when the island area is formed along X axis, the second antenna conducts communication by unidirectional polarization, while in the case where the island area is formed along X and Y axes, the second antenna conducts communication by bidirectional polarization.

5. The REID tag according to claim 1, wherein a U-shaped groove is formed in the surface of the metal foil and the space pattern forms the second antenna by a peninsular area defined by the U-shaped groove.

6. The REID tag according to claim 5, wherein the second antenna formed by the peninsular area has an electrical length of $\lambda/4$, where $\lambda$ is the wavelength of the radio wave radiated from the small antenna.

7. A REID tag according to claim 1,
    wherein the space pattern implements the second antenna by forming a slot having a predetermined length and a predetermined width on the surface of the metal foil.

8. A REID tag according to claim 7,
    wherein the slot formed on the surface of the metal foil has an electrical length of $\lambda/2$ or $\lambda/4$, where $\lambda$ is the wavelength of the radio wave radiated from the small antenna.

9. A REID tag according to claim 8,
    wherein the electrical length of the slot is $\lambda/2$ for the unidirectional polarization of the second antenna and $\lambda/4$ for the bidirectional polarization of the second antenna.

10. A REID tag according to claim 7,
wherein the slot is in the shape of selected one of a straight line, L, S and arc.

11. A REID tag according to claim 7,
wherein the IC chip is mounted along the width of the slot in the neighborhood of the longitudinal central portion of the slot.

12. A REID tag according to claim 1,
wherein the metal foil is an aluminum sheet used as a package of an article.

13. A REID tag according to claim 12,
wherein the package is configured by attaching the aluminum sheet and the resin sheet to each other, and the inlet is mounted on selected one of the island area, the peninsular area and the upper portion of the slot through the resin sheet.

14. A REID tag according to claim 13,
wherein the inlet is fixed on the surface of the resin sheet by selected one of an adhesive and a pressure sensitive adhesive.

15. A REID tag according to claim 14,
wherein in the case where the base material of the inlet is thinner than a predetermined thickness, a resin substrate is interposed on the reverse surface of the inlet.

16. A REID tag according to claim 15,
wherein the resin substrate is formed of selected one of materials including PVC, PET, PP and PE and a formed version of any of the materials.

17. A REID tag according to claim 15,
wherein the total thickness of the base material of the inlet and the resin substrate is 0.05 mm to 0.20 mm.

18. A REID tag according to claim 1,
wherein the small antenna has the width of 1.5 mm and the length of not more than 10 mm.

19. The REID tag according to claim 1, wherein said space pattern is formed by die pressing.

20. The REID according to claim 1, wherein said resin sheet is a PVC sheet.

21. A method of manufacturing a package film including a REID tag for transmitting the information recorded in an inlet including an IC chip mounted on a small antenna having a slit therein by radio communication, wherein the package film is constituted of a lamination of at least a PVC and metal sheet, the method comprising the steps of:
    forming a space pattern including an aperture through the metal sheet to produce a second antenna in a portion of the metal sheet,
    wherein as a result of forming the space pattern including the aperture, a protrusion is formed on a resin sheet; and
    mounting the inlet on the second antenna to provide a REID tag comprised of the inlet and the second antenna.

22. The method of manufacturing a package film according to claim 21, wherein in the step of forming a space pattern, said space pattern is formed by cutting out a portion of said metal sheet.

23. The method of manufacturing a package film according to claim 21, wherein said resin sheet is a PVC sheet.

* * * * *